US010155053B2

(12) United States Patent
Carrazana et al.

(10) Patent No.: US 10,155,053 B2
(45) Date of Patent: Dec. 18, 2018

(54) METHOD FOR OBTAINING NOVEL DERIVATIVES OF NAPHTHALENE FOR THE IN VIVO DIAGNOSIS OF ALZHEIMER'S DISEASE

(71) Applicants:Marquiza Sablon Carrazana, Ciuda de la Habana (CU); Chryslaine Rodriguez-Tanty, Ciuda de la Habana (CU); Alejandro Perera Pintado, de Octubre Cuba (CU); Suchitil Rivera Marrero, Pinar del Rio (CU); Rafaela Perez Perera, Ciudad de la Habana (CU); Rosa Maria Lopez Barroso, Ciudad de la Habana (CU); Anais Prats Capote, Ciudad de la Habana (CU); Herman Velez Castro, Ciudad de la Habana (CU); Carlos Serafin Perez Martinez, Ciudad de la Habana (CU); Pedro Valdes Sosa, Ciudad de la Habana (CU)

(72) Inventors: Marquiza Sablon Carrazana, Ciuda de la Habana (CU); Chryslaine Rodriguez-Tanty, Ciuda de la Habana (CU); Alejandro Perera Pintado, de Octubre Cuba (CU); Suchitil Rivera Marrero, Pinar del Rio (CU); Rafaela Perez Perera, Ciudad de la Habana (CU); Rosa Maria Lopez Barroso, Ciudad de la Habana (CU); Anais Prats Capote, Ciudad de la Habana (CU); Herman Velez Castro, Ciudad de la Habana (CU); Carlos Serafin Perez Martinez, Ciudad de la Habana (CU); Pedro Valdes Sosa, Ciudad de la Habana (CU)

(73) Assignee: CENTRO DE NEUROCIENCIAS DE CUBA, Havana (CU)

( * ) Notice: Subject to any disclaimer, the term of this patent is extended or adjusted under 35 U.S.C. 154(b) by 399 days.

(21) Appl. No.: 14/636,316

(22) Filed: Mar. 3, 2015

(65) Prior Publication Data
US 2015/0217005 A1 Aug. 6, 2015

Related U.S. Application Data

(62) Division of application No. 13/574,050, filed as application No. PCT/CU2010/000001 on Apr. 17, 2010.

(51) Int. Cl.
| | | |
|---|---|---|
| A61K 51/00 | (2006.01) | |
| A61M 36/14 | (2006.01) | |
| A61K 51/04 | (2006.01) | |
| C07C 43/225 | (2006.01) | |
| C07C 233/07 | (2006.01) | |
| C07C 233/36 | (2006.01) | |
| C07C 233/47 | (2006.01) | |
| C07C 323/25 | (2006.01) | |
| C07D 207/06 | (2006.01) | |
| C07D 207/46 | (2006.01) | |

(52) U.S. Cl.
CPC ...... *A61K 51/0446* (2013.01); *A61K 51/0402* (2013.01); *A61K 51/0482* (2013.01);
(Continued)

(58) Field of Classification Search
CPC ............ A61K 51/0446; C07B 2200/05; C07C 43/225
(Continued)

(56) References Cited

U.S. PATENT DOCUMENTS

| | | | | |
|---|---|---|---|---|
| 6,114,175 A | * | 9/2000 | Klunk | A61K 49/06 424/1.11 |
| 6,379,650 B1 | * | 4/2002 | Ashton | A61K 51/0497 424/1.11 |
| 2007/0166227 A1 | * | 7/2007 | Liu | A61K 51/0423 424/1.11 |

FOREIGN PATENT DOCUMENTS

WO WO 0010614 A1 * 3/2000 ......... A61K 51/0406

OTHER PUBLICATIONS

Agdeppa et al. Neuroscience 117 (2003) 723-730.*
(Continued)

*Primary Examiner* — Michael G. Hartley
*Assistant Examiner* — Sean R Donohue
(74) *Attorney, Agent, or Firm* — Lackenbach Siegel, LLP (57) ABSTRACT

This invention relates to a chemistry branch, particularly to the field of compounds' organic synthesis that belong to the aromatic bicyclic or naphthalene category, used in the detection of amyloid sheets. These new naphthalene derivatives have a general formula: Wherein R represents mutually independent groups. In I: $R_1$: -alkylenyl-C(O)NH-alkylenyl-$R_3$, -alkylenyl-C(O)O—$R_4$, $R_3$: —COOH, —OH, —SH, —$NH_2$, -alkyl-NH-alkyl-N-dithiocarbamate alkaline earth metal salts, $R_4$: H, succinimidyl group, $R_2$: —H, -alkyl. In II: $R_1$: -alkyl, -alkylenyl-halide-alkylenyl-hydroxyl-alkylenyl-O-aryl, —O-alkylsulfonate alkylenyl, $R_2$: -halide-alkylenyl-O-aryl, -alkylenyl-O-alkylsulfonate, -alkylenyl-halide-, —CH(O), —HC=C(CN)$_2$, —HC=CHNO$_2$, -alkylenyl-NH$_2$, -alkylenyl-NH-alkyl, -alkylenyl-alkyl-N-dithiocarbamate alkaline salts. The terms "alkyl" and "alkylenyl" refer to linear or branched aliphatic chains, preferably from 1 to 4 carbon atoms and the term halide to fluorine, bromine or iodine. These compounds are neutral, lipophilic and have low molecular weight and therefore they cross the blood brain barrier and attach to the amyloid sheets. The present invention provides procedures for obtaining naphthalene derivatives with good yields, which can be practical, economical and adapted to a larger-scale manufacturing.

18 Claims, 3 Drawing Sheets

(52) U.S. Cl.
CPC .......... *C07C 43/225* (2013.01); *C07C 233/07* (2013.01); *C07C 233/36* (2013.01); *C07C 233/47* (2013.01); *C07C 323/25* (2013.01); *C07D 207/06* (2013.01); *C07D 207/46* (2013.01); *C07B 2200/05* (2013.01)

(58) Field of Classification Search
USPC ...................................................... 424/1.81
See application file for complete search history.

(56) References Cited

OTHER PUBLICATIONS

Zhang et al. Curr. Top. Med. Chem. 2007, 7, 1817-1828.*
Miranda et al. Toxic. In Vitro 1991, 5, 451-455.*
Pietzsch et al. Inorganica Chimica Acta 165 (1989) 163-166.*

* cited by examiner

METHOD FOR OBTAINING NOVEL DERIVATIVES OF NAPHTHALENE FOR THE IN VIVO DIAGNOSIS OF ALZHEIMER'S DISEASE

PRIOR RELATED APPLICATIONS

This application is a divisional application of U.S. patent application Ser. No. 13/574,050, filed Aug. 23, 2012, which claims priority to PCT Patent Application No. PCT/CU2009/000057, filed Apr. 17, 2009, and PCT Patent Application No. PCT/CU2010/000001, filed Apr. 17, 2010 and incorporates the above-referenced applications in their entireties by reference thereto.

DESCRIPTION OF THE INVENTION

The present invention is related to the branch of chemistry, particularly with obtaining new naphthalene derivatives and its labeling with radionuclides used in nuclear medicine for imaging diagnostic, which includes gamma ray emitters such as technetium 99 metastable ($^{99m}$Tc), iodine 123 or 131 ($^{123}$I or $^{131}$I) and others, as well as positron emitters: fluorine 18 ($^{18}$F), carbon 11 ($^{11}$C), oxygen 15 ($^{15}$O) and others, with the aim of displaying neuropathological deposits in the brain through images from nuclear medicine and providing early diagnosis of Alzheimer's disease or other diseases that might be associated with the presence of these neuro-deposits (such as rheumatoid arthritis and others).

Alzheimer's disease (AD) affects about 20 to 40% of the elderly population. It is estimated that, at a global scale, 18 to 22 million people suffer from AD or a related dementia, and it will reach 34 million by 2020. This condition is characterized by the presence of neuropathology deposits in the brain (senile sheets and neurofibrillary tangles), which are involved in the process leading to progressive neuronal degeneration and neuronal death. The neurofibrillary tangles (NFT) are fibrillar aggregates of hyperphosphorylated tau protein and are located within neuronal cells. In contrast, senile sheets are found outside them and consist primarily of deposits of β-amyloid peptides (39-42 amino acids). Gong et al., Proc. Natl. Acad. Sci USA 2003, 10 (18), 10417-22.

The clinical diagnosis of AD has a moderate reliability and often lacks sensitivity and specificity. Ball et al., in Neurobiol. Aging. 1997, 18 (4), S1-2, suggests that its definitive diagnosis is made post-mortem through neuropathological examination with the discovery of senile sheets and/or neurofibrillar tangles in neocortical brain sections, which are displayed through staining (colorimetric or fluorescent) with Congo Red (CR), thioflavin or Chrysamine-G. Since the histopathologic appearance of these structures occurs long before the disease symptoms appear, it is valuable to count with a means of early and in vivo diagnosis that allows visualizing the same and that also facilitates monitoring the effectiveness of the therapeutic treatments.

For this purpose, non-invasive methods made through genetic tests, immunoassays and imageneology techniques are under study. In particular, the latter are very favourable, for both, the AD diagnosis and other neurological diseases linked to the presence of neurofibrillary tangles and amyloid sheets, such as: Parkinson's, Down syndrome, hereditary cerebral hemorrhage associated with amyloidosis Dutch type and other diseases associated with amyloidosis.

Neuroimaging techniques include: Positron Emission Tomography (PET), Single Photon Emission Computer Tomography (SPECT) and Magnetic Resonance Imaging (MRI). Volder et al., Developmental Science, 2002, 5 (3), 344-60.

To implement the PET technique, it has used different markers utilized in the in vitro detection of amyloid structures, such as Congo Red, thioflavin and Chrysamine-G analogs, but with unsatisfactory results. Zhen et al., J. Med Chem, 1999, 42, 309-24; Dezutter et al., Eur. J. Nucl. Med, 1999, 26, 1392-99.

Other compounds tested, such as 1-(6[2-[$^{18}$F]fluorethyl) (methyl)amino]naphthalene-2-yl) ethanone ($^{18}$F-FENE) and 2-(1-(6-[(2-[$^{18}$F]fluorethyl)(methyl)amino]-2-naphthyl) ethyl)malononitrile ($^{18}$F-FDDNP, Barrio et al. in WO00010614, WO2005040337 and US2004072371; Kepe et al. in WO2006083378 and Agdeppa et al., 2001, J. Neurosci., 21, 24, 189) labelled with the isotope fluorine 18 (t½=109.8 min), which have been used in the in vivo detection of pathological deposits of AD and detected with the PET technique. It has also been described by Small et al. N. Engl. J Med 2006, 355, 25, 2652-63, that it is possible to differentiate patients with cognitive impairment from those with AD.

Other compounds have also labeled with fluorine 18 or carbon 11 (t½=20.4 min), which are derived from benzothiazole, imidazole, stilbene, acridine or styrylbenzoxazol with few promising results. The use of PET visualization technique is limited by: the high cost of equipment, type of isotope used are generated in a cyclotron located within the nuclear medicine service or close to it and the short disintegration period, which requires that the labelled radiopharmaceuticals with them must be used immediately.

Moreover, imaging SPECT technique is more advantageous since its equipment is less expensive and the generation and prices of the isotopes are more affordable, allowing this technique to be more widespread.

In particular, technetium 99m ($t_{1/2}$=6.02 h., Eγ=140 keV) is used in more than 80% of routine nuclear medicine diagnosis because it can be used in low doses and therefore the patient receives less radiation. Furthermore, it is obtained from a generator of $^{99}$Mo/$^{99m}$Tc, which is available on the market at relatively cheap prices. This radioisotope has as special feature that is able to form stable complexes with organic compounds related to biological structures, presenting donor atoms. All these advantages point to the need of including a diagnosis, which may be used in SPECT technique, which is reliable for quantification and visualization of amyloid deposits in the brain.

There are numerous patents relating to the use of $^{99m}$Tc as a marker to diagnose various brain pathologies. Among them is the invention of Li-Han et al. (TW438596) which describes the production of Tropane radiopharmaceutical $^{99m}$Tc-TRODAT as selective marker of the dopamine transporter, for the detection of presynaptic neuronal degeneration in Parkinson's disease, without ruling out other diseases such as AD. Furthermore, Zhu et al. in CN1072020 describes a complex of $^{99m}$Tc-ethylcysteinate diethyl ester (ECD), which crosses the blood brain barrier and it is used for cerebral perfusion studies. With this aim, they have studied other neutral and lipophilic complexes of $^{99m}$Tc-containing functional groups of amide, amine, thioether, thiol and oximes especially of the propylamineoximine type (EP0194843, GB8426845D0, EP0123504, EP0229718 and U.S. Pat. No. 5,690,904). In general, these patents describe procedures for obtaining suitable ligands for the $^{99m}$Tc, in order to improve retention of the complex in the brain, and their in vivo stabilities and guarantee a good SPECT image quality. However, using these complexes of $^{99m}$Tc for the diagnosis of AD has had unsatisfactory results.

Specifically, for the early diagnosis of AD, the aforementioned pigments have been marked with $^{99m}$Tc, $^{123}$I or $^{11}$C, used for amyloid structures postmortem staining, such as the Congo Red and its benzothiazoles and benzidine derivatives (U.S. Pat. No. 5,008,099, U.S. Pat. No. 6,114,175, U.S. Pat. No. 6,133,259, U.S. Pat. No. 6,417,178). These radiopharmaceuticals have shown favourable results in studies in vitro, but failed in vivo diagnosis. In addition, Klunk et al. in U.S. Pat. No. 6,168,776 argue that many of these compounds have carcinogenic properties.

Other Congo Red complexes with $^{99m}$Tc labeled are described in U.S. Pat. No. 6,379,650 by Wesley et al., where they obtained neutral and lipophilic ligands using diamine dithiolates. However, these complexes do not cross the blood-brain barrier due to the presence of sulphonic groups and their high toxicity.

Sharma et al. US2006039859 describes a variation in the use of Congo Red, which is used to label peptides. These new derivatives are capable of crossing the blood brain barrier and bind to the amyloid structures. As an extension of the patent, it is reported that the peptide portion of these derivative functions as a ligand of $^{99m}$Tc. However, the results described are unsatisfactory which may be due to the high molecular weight of the complexes in question.

Other types of molecules that bind specifically to the deposition of insoluble amyloid protein, are styrylbencenes derivatives (Zhuang et al., J. Med. Chem, 2001, 44, 12, 1905-14) and pyridine (Kung et al., Mol. Imaging Biol, 2003, 5, 6, 418-26). In particular, derivatives of stilbene showed by Kung et al. in WO03018070 and WO2006066104 have been effective as inhibitors of amyloid aggregation. However, as described by these authors in Nucl. Med Biol, 2005, 32, 2, 171-84, conjugates of these compounds with $^{99m}$Tc have not shown favourable results for the in vivo detection of AD.

It is known, following epidemiological studies, that the use of non-steroidal anti-inflammatory drugs reduce the relative risk of developing AD, among them is naproxen, which count with a naphthalene ring (Agdeppa et al., 2003 Neurosciences, 117, 723-30).

On this basis, naphthalene rings present in the Congo Red have been susceptible to chemical modifications, for the purpose of evaluating these compounds for in vivo diagnosis of AD. So, Steven et al. in U.S. Pat. No. 4,933,156 show, among others, the first derivative of Congo Red identified for this purpose, marked with radioactive isotopes of iodine. Moreover, Kung et al. described in US2006051293 the thioflavin derivatives which may have substituent groups such as naphthyl, among others, and which are able to form lipophilic neutral complexes with $^{99m}$Tc. Also Gallo et al. refer in WO200603 the use of pamoic acid, its derivatives and analogues, for the treatment of diseases characterized by deposition of amyloid aggregates. In particular, pamoic acid is a derivative of naphthoic acid, which has in its structure two rings of naphthalene and forms complexes with radioactive isotopes such as indium, gadolinium and technetium. In short, in these patents compounds described are obtained through complex and laborious synthesis procedures, from expensive raw materials.

Minetti et al. in WO2007045593 describes other naphthyl derivatives, which also inhibit amyloid aggregation and, according to its inventors, surprisingly, cross the blood brain barrier. These compounds, besides being present in pharmaceutical compositions for treating this condition, can also be used for diagnosis through different imaging techniques. In this case, one element of the compounds structure is replaced by a carbon, hydrogen or oxygen radioactive isotope, or they also form stable compounds with radioisotopes of iodine, indium, gadolinium or technetium.

In the application WO02075318 of Wischik et al. is presented a method for determining neurofibrillary degeneration associated to tautopatia, as manifested in AD, which describes new ligands of sulphonated benzothiazol type. This invention claimed ligands with groups that form complexes with technetium and also one of the proposed formulas has naphthyl as a substituent group, among others. Similarly, Hays et al. in WO9716194 describes some naphthyl-azo compounds, which inhibit amyloid aggregation and can be labeled with radioisotopes to diagnose. However, there is no data or examples of in vivo experiments that support this application and there is no reference in the claims to a particular radioisotope.

The present invention relates to derivatives of naphthalene, which show hydrophobic properties and are therefore able to cross the blood brain barrier and are related to characteristic pathological biostructures of AD. In addition, these compounds have the function of forming stable compounds with gamma ray emitters such as technetium 99 metastable ($^{99m}$Tc), iodine 123 or 131 ($^{123}$I or $^{131}$I) and others, as well as positron emitters: fluorine-18 ($^{18}$F), carbon 11 ($^{11}$C) and oxygen 15 ($^{15}$O) and others. Also, these compounds may bear appropriate functional groups, such as fluorine-19 atom, which allow the obtaining of nuclear magnetic resonance imaging. The visualization of these marked biostructures is done with the proper instrumentation for each case, which allows observing and quantifying the distribution of the labeled compound within the brain. An extension of this invention's object is that it provides synthesis procedures of a series of hydrophobic compounds labeled with gamma emitters or fluorine 19 ($^{19}$F). Another object of this invention is that these compounds can be used as diagnosis of diseases characterized by the appearance of amyloid tissue. They can be used as therapeutic agents of the aforementioned diseases.

This invention provides novel derivatives of naphthalene and its obtaining procedures through chemical synthesis. In particular, these new compounds are characterized by crossing the blood brain barrier and bind selectively to the senile sheets that appear in Alzheimer's disease. The present invention involves obtaining derivatives that correspond to the structures I and II.

In structures I and II the R terms are independent.

Wherein I: $R_1$: is selected from the group alkylenyl-C(O)NH-alkylenyl-$R_3$, -alkylenyl-C(O)O—$R_4$. $R_3$: is selected from the group —COOH, —OH, —SH, —NH$_2$, -alkyl-NH, -alkyl-N-dithiocarbamate alkaline earth metal salts. $R_4$: is selected from the H group, succinimidyl group, $R_2$: is selected from the group —H, -alkyl.

Wherein II: $R_1$: is selected from the group -alkyl, -alkylenyl-halide, -alkylenyl-hydroxyl, -alkylenyl-O-arylsulfonate, alkylenyl-O-alkylsulfonate; $R_2$: is selected from the group -halide, -alkylenyl-O-arylsulfonate, -alkylenyl-O-alkylsulfonate, -alkylenyl-halide, —CH(O), —HC=C(CN)$_2$, —HC=CHNO$_2$, -alkylenyl-NH$_2$, -alkylenyl-NH-alkyl, -alkyl-alkylenyl-N-dithiocarbamate salts such as cesium, potassium or sodium.

In both structures, the term "alkyl" refers to a straight or branched aliphatic chain, of saturated carbon and hydrogen atoms, preferably methyl, ethyl, n-propyl, iso-propyl, n-butyl or iso-butyl. The "alkylenyl" term refers to a divalent analog of a linear or branched alkyl group, preferably ethylenyl (—CH$_2$CH$_2$—), propylenyl (—CH$_2$CH$_2$CH$_2$—)

or butylenyl (—CH$_2$CH$_2$CH$_2$CH$_2$—). The term "halide" refers to fluorine, bromine or iodine.

The present invention also includes tautomeric forms, geometric and optically active isomers and enantiomers, diastereomers and racemic mixtures of compounds defined by the structures I and II.

Figure 1:
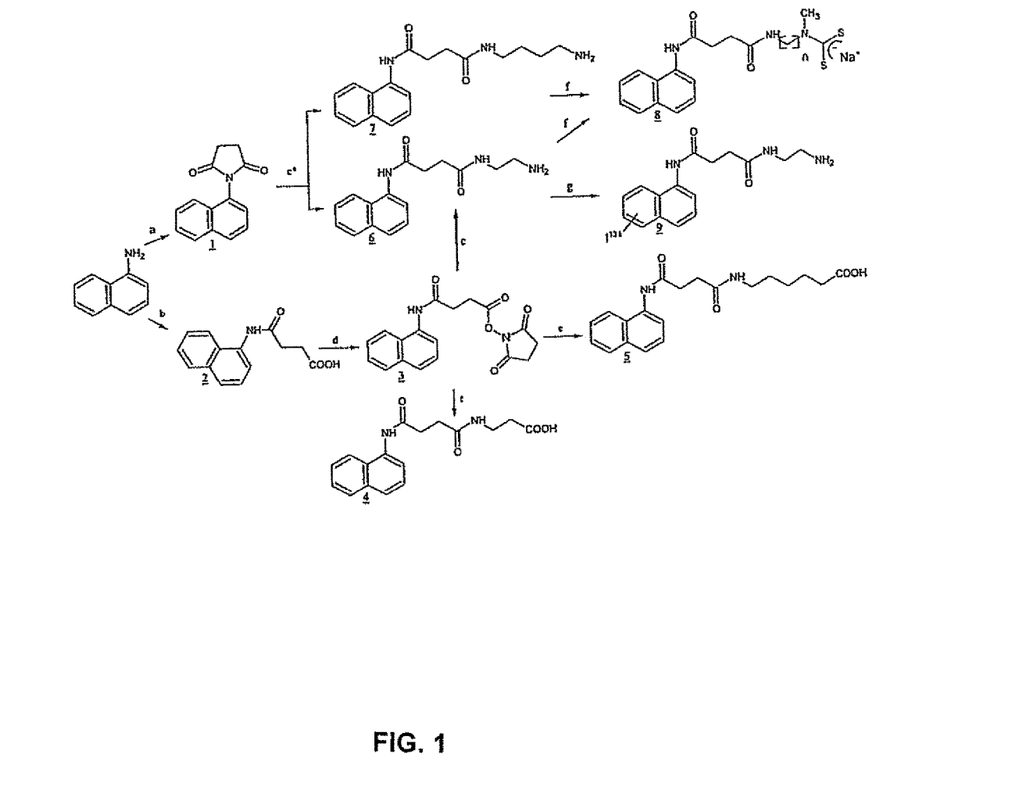
FIG. 1 shows the general procedure for synthesis of derivatives 1-naphthyl derivatives with structure I, which includes the most relevant reaction conditions (a: succinic anhydride, NMM; b: succinic anhydride, c, c *: ethylenediamine or 1,4-butylenediamine d: NHS, DCC, e: 6-aminocaproic acid or 1-alanine, f: a) $CH_3I$, base, b) $CS_2$, CsOH; g: Iodogeno in $CHCl_3$ ($^{131}I$).
Figure 2:
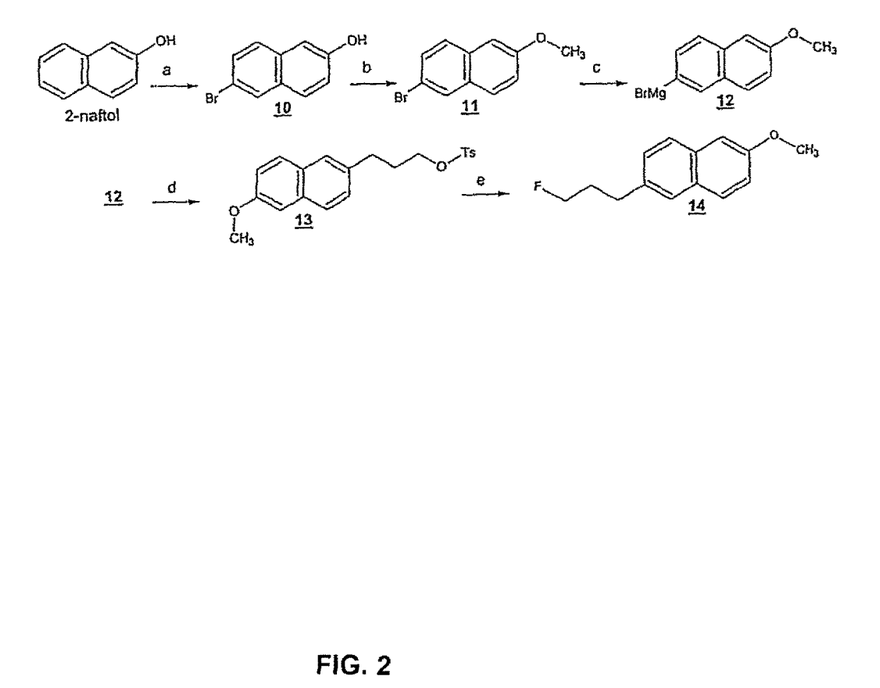
FIG. 2 shows the general procedure of synthesis of 2,6-naphthyl derivatives with structure II, which includes the most significant reaction conditions (a: $Br_2$, Sn, glacial acetic acid; b: dimethylsulfate, base, acetone; c: Mg, THF, Ar, d: 1,3-propanediol di-p-tosylate (PrDiTs) $Li_2CuCl_4$, THF, Ar; e: 1-butyl-3-methylimidazolium tetrafluoroborate, CsF, $CH_3CN$).

This invention has, as one of its objectives, to provide synthesis general procedures for obtaining new derivatives of naphthalene with good yields, as it is illustrated in FIGS. 1 and 2, which should not be regarded in any way as a constrain of the present invention. The procedures are practical, inexpensive and can be adapted to manufacturing at a larger scale.

In general, FIG. 1 shows the compounds with structure I, which can be obtained from the naphthylamine raw material very accessible in the market. In principle, the naphthylamine reacts with succinic anhydride in the presence or absence of a tertiary amine (whose pKa is between 4 and 8, preferably N-methylmorpholine), to form compounds 1-(1-naphthyl)-2,5-pyrrolidinone (1, step a) or 4-(1-naphthylamine)-4-oxobutanoic acid (2, step b), respectively. Obtaining these compounds allows introducing, through various reactions, spacer arms in position α-(or 1-) of naphthalene molecule. With the same purpose, it is also obtained the 4-(1-naphthylamino)-4-oxobutanoic acid, N-hydroxysuccinimide ester (3, step d). The condensation reaction of 2 with N-hydroxysuccinimide (NHS) occurs in presence of a condensing agent like dicyclohexylcarbodiimide (DCC) and preferably with anhydrous 1,4-dioxane as solvent. In this synthesis is obtained a high yield without the need of purifying product 3 for later use.

Then, the naphthyl derivative 3 is used as acylating agent. The compound 3 is selective for primary amino groups, such as linear or branched aliphatic diamines (ethylenediamine, propylenediamine, 1-methyl-1,2-ethylenediamine, butylenediamine) and polyfunctional amines such as α-amino acids; thioamines, amino alcohols and aminocarboxylic acids (α-aminoisobutyric acid, 2-aminoethanethiol, ethanolamine, β-alanine, 6-aminohexanoic acid, etc.). The reaction conditions are mild (temperature, solvent, time, etc.) and generate no corrosive waste. Finally, with this reaction a further lengthening of the carbon chain of spacer arm is achieved so as to obtain the following new compounds: 4, 5 (step e), 6 and 7 (step c).

These compounds can also be obtained by a new procedure through a one-pot technique, which is an innovation. With this purpose the compound 3 is obtain in situ, then it reacted with an excess of diamine (e.g. ethylenediamine and butylenediamine) or a aminocarboxylic acid (e.g. β-alanine and 6-aminohexanoic acid) to obtain derivatives 4, 5, 6 and 7, which carry an acid or amino terminal group. Specifically, the excess of the diamine is to ensure that no side products are formed such as diamines N,N'-disubstituted, leading to a dramatic decrease in the synthesis yield. The reaction is carried out at room temperature and in the presence of an organic solvent, preferably anhydrous 1,4-dioxane, to obtain good yields.

In the same way and with similar yields, derivatives 6 and 7 are obtained from the reaction of the naphthyl derivative (1) with the diamine excess (step c *, FIG. 1) at reflux and in the presence of an organic solvent, anhydrous preferably 1,4-dioxane or DMF. So far, we have not found reports of these compounds in literature.

This patent also shows the procedure for obtaining derivatives 8 (step f, FIG. 1), from the reaction of N-alkylation (step f-a) of the previously described amino-terminal derivatives (6 and 7), in the presence of different alkylating agents (CH$_3$I, C$_2$H$_5$Br, (CH$_3$)$_2$SO$_4$, (C$_2$H$_5$)$_2$SO$_4$), inorganic bases (K$_2$CO$_3$, Cs$_2$CO$_3$, CsOH) and solvents (acetone, DMF). These new alkyl derivatives (described example: compound 8a) react with CS$_2$ in the presence of CsOH, producing dithiocarbamate compounds (stage f-b). They can be used as potential ligands of the $^{99m}$Tc, like its synthetic precursors the alkylamino derivatives.

The iodine labeling methods are classified into direct or indirect, according to the type of bond established between the iodine and the compound to be marked. In direct methods, radioactive iodine is easy incorporated with high efficiency to the aromatic ring of organic compounds. In this invention this procedure is used to label the compound 6 (step g, FIG. 1), specifically through the Iodogeno or chloramide method (Saha on Fundamentals of Nuclear Pharmacy. Radiopharmaceutical and Methods of Radiolabeling. Fourth Ed Springer-Verlag, USA. 1998, p.: 93-97). This procedure has a labeling efficiency ranging between 70 and 80% and high specific activity since there is no isotope or sample dilution. This labeling procedure can be extended to other molecules described here that have another spacer arm. We are not aware of literature reports regarding these labeled compounds.

On the other hand, the compounds with structure II can be obtained from the affordable 2-naphthol raw material. The general procedure shown in FIG. 2, which consists of 5 stages of synthesis, specifically aims to introduce a monofluorinated alkyl chain in position 6- of the 2-methoxynaphthalene.

The first stage is the bromination of 2-naphthol (pKa 9.23) carried out through a procedure already described by Koelsch in Organic Synthesis, Coll., 1955, 3, 132 and Reddy et al., in Organic process research and Development, 1999, 3, 121-25. Thus, the 2-naphthol reacts with molecular bromine in presence of glacial acetic acid as solvent and Sn as reducing agent of the 1,6-dibromo-2-naphthol intermediate, which is in situ formed. This reduction is selective due to the dibrominated derivative thermodynamic instability leading to 6-bromo-2-naphthol (10).

The step b of FIG. 2 is the reaction of O-alkylation of 10 to obtain the 6-bromo-2-methoxynaphthalene (11). Reddy et al. described this procedure in Organic Process Research and Development, 1999, 3, 121-25, from the reaction between 10 and dimethylsulfate as alkylating agent in the presence of K$_2$CO$_3$ as base and a mixture of acetone-water as solvent, at 60° C. However, under these conditions the degree of conversion is very low, even though DMF or acetone are used as solvents and the reaction is refluxed for 3 to 72 hours. The use of cesium bases (CsOH and Cs$_2$CO$_3$) compared to their counterparts in Li$^+$, Na$^+$, K$^+$ and Rb$^+$, is currently reported in the alkylation reactions due to the so-called "cesium effect". (Welton in Chem Rev., 1999, 99, 2071-83; Kim et al. in J. Am. Chem. Soc. 2002, 124, 10278-9; Gerstenberger et al. in Angew. Chem. Int. Ed. Engl., 1981, 20, 647-67). In this invention, Cs$_2$CO$_3$ base are successfully used in the reaction of O-alkylation of 10 with different alkylating agents (alkyl sulfates, alkyl halides, alkyl dihalides). The reaction occurs rapidly with dimethylsulfate in acetone (as solvent) at room temperature. The yield of compound 11 is practically quantitative. We are not aware that these compounds of cesium, in particular Cs$_2$CO$_3$, are used for the reaction conditions described.

In the third stage of synthesis (step c, FIG. 2) 11 reacts with Mg in the presence of iodine traces to obtain the Grignard reagent (12), according to general procedure described by Kidwell et al. (Organic Synthesis, Coll., 1973, 5, 918). This intermediate is not isolated and it is subsequently used in cross-coupling reaction (step d). In the present invention, this synthesis is performed, in general, from a reaction of an aryl magnesium with a halide or an alkyl sulfonate and a copper complex as catalyst. In this procedure, carried out in an inert atmosphere, the order of the reagent addition and temperature play an important role. Specifically, if it is added the Grignard reagent 12 to the mixture of 1,3-propanediol di-p-tosylate with the copper catalytic ($Li_2CuCl_4$ or $Li_2CuCl_3$) which is between −70° C. to −15° C., 3-(6-methoxy-2-naphthyl)propyl 4-methylbenzenesulfonate (13) is obtained with good yields. This new compound, 13, is a valuable intermediate in the next synthetic stage which is an innovation of this patent.

The fourth stage of synthesis (step e, FIG. 2) refers to the obtaining of a fluorinated derivative, based on studies by Kim et al. in J. Org. Chem, 2003, 68, 4281-5. This nucleophilic substitution reaction occurs with the use of an alkali metal fluoride (KF, CsF and RbF) in the presence of an ionic liquid, such as 1-n-butyl-3-methylimidazolium (bmim) ($BF_4^-$, $PF_6^-$, $SbFs_6^-$, triflate [OTf], bis(trifluoromethanesulfonyl)imide [$NTf_2^-$], $OAc^-$) and acetonitrile as solvent. In this invention, the reaction takes place with 13 preferably, in the presence of CsF and (bmim) ($BF_4^-$) to obtain the new derivative 2-(3-fluoropropyl)-6-methoxynaphthalene (14).

Chemical compounds that cross the blood brain barrier (BBB) should be neutral and lipophilic and also, have a low molecular weight. The partition coefficient (P) provides a measure of the compound lipophilicity and is closely related to drug distribution in the body, its absorption in tissues and its route of excretion (Meade et al. in Curr. Opin. Neurobiol., 2003, 13, 5, 597-602). One method used to determine this parameter is that of radiotracers which relates the radiotracer's activity or number of counts in the octanol organic phase with that of the aqueous phase. In this invention the compounds labeling is carried out using the Iodogeno method ($^{131}I$).

According to studies Dischino et al. (The Journal of Nuclear Medicine, 1983, 24, 11, 1030-38), the optimal values of partition coefficient, which ensure that the compound crosses the BBB, are in the range of 0.9 to 2.5. On the other hand, there has been established by J. Levin in Med. Chem., 1980, 23, 682-84, that to cross the BBB by passive diffusion, the molecular weight values must range between 400 and 657 Da. In this invention, the synthesized compounds have values of molecular weights between 200 and 450 Da, and their partition coefficients, expressed as log P measured in octanol/water, range between 2.1 and 2.5.

The current invention shows that the synthesized compounds have values of molecular weights and partition coefficients that correspond to the values set for other compounds that cross the BBB. In summary, the compounds described herein, have the advantage of being used as staining agents of amyloid plaques present in AD as they show correspondence with these parameters.

Figure 3:
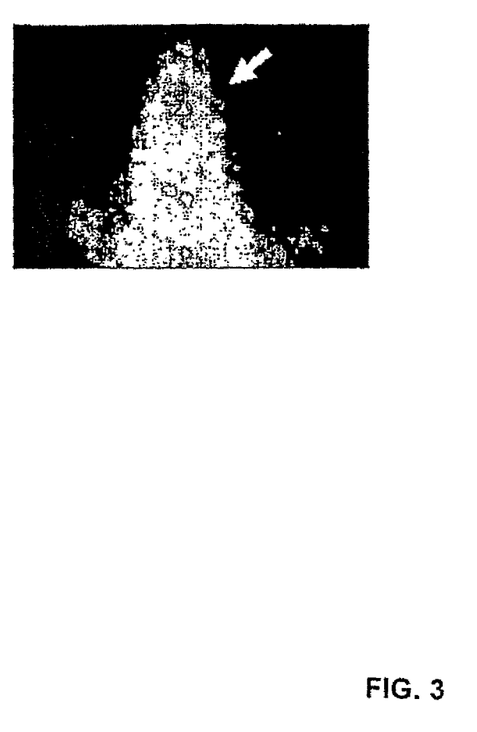
FIG. 3 shows the distribution of the N1-(2-aminoethyl)-N4-(1-naphthyl) succinimide (6) compound labeled with $^{131}I$ in rats, after its intravenous injection. The arrow indicates the detection of the compound in the region of interest (maximum uptake at about 3 min.).

In this invention the compositions of naphthalene derivatives labeled with $^{131}I$, injected into rats, rapidly cross the blood brain barrier and have an appropriate retention time. As non-limiting example, FIG. 3 shows the distribution in rats of compound 6 labeled with $^{131}I$, (9) after its intravenous injection. Thus, an arrow indicates the detection of the compound in the region of interest (maximum uptake at about 3 min.) and then starts the slow excretion of the radioiodinated compound.

The obtaining procedures of naphthalene derivatives showed in the present invention are further illustrated by the following examples, which should not be regarded in any way, as constrain of the present invention. The compounds obtained were also appropriately characterized by spectroscopic techniques such as IR, $^1H$ and $^{13}C$ NMR and Mass.

DESCRIPTION OF THE EMBODIMENTS

Example 1: 1-(1-naphthyl)-2,5-pyrrolidinedione (1)

1-naphthylamine (5 g, 34.96 mmol) was dissolved in 50 mL of anhydrous 1,4-dioxane. Succinic anhydride (6.99 g, 69.92 mmol) and N-methylmorpholine (NMM, 7.6 mL, d=0.92 g/mL, 69.92 mmol) were added. The reaction mixture was heated at reflux for 5 hours. Once the reaction is completed (TLC), the solvent is removed by rotoevaporation. The solid residue is re-dissolved and re-crystallized from ethanol to obtain 5.2 g of compound 1 (Yield: 66%). Mp.: 153.5-154.5° C. (Lit: 153° C.). ESI-MS (m/z)=226 $(M+1)^+$.

Example 2: 4-(1-naphthylamino)-4-oxobutanoic acid (2)

1-naphthylamine (10 g, 69.84 mmol) and succinic anhydride (13.96 g, 140 mmol) were dissolved in 100 mL of anhydrous 1,4-dioxane. The reaction mixture was refluxed for 2 h and later, cooled to precipitate a violet solid which was filtered and washed with 1,4-dioxane. Recrystallization from ethanol gave 15.82 g of white solid. Yield: 93%. Mp.: 167-169° C. ESI-MS (m/z)=244 $(M.+1)^+$.

Example 3: 4-(1-naphthylamino)-4-oxobutanoic acid, N-hydroxysuccinimide ester (3)

Compound 2 (2 g, 8.23 mmol), N-hydroxysuccinimide (NHS) (1.42 g, 12.34 mmol) and dicyclohexylcarbodiimide (DCC) (2.54 g, 12.33 mmol) were dissolved in 32 mL of anhydrous 1,4-dioxane. The reaction mixture was refluxed for 3 h. and then cooled at room temperature in order to remove the dicyclohexylurea (DCU) formed. The filtrate was rotoevaporated and cooled to separate by filtration a white solid that was washed with plenty of water and diethyl ether, and air-dried to obtain 2.29 g of product. Yield: 87%, Mp.: 168-171° C. ESI-MS (m/z)=341 $(M.+1)^+$.

Example 4: N-[4-(1-naphthylamino)-4-oxobutanoyl]-β-alanine (4)

Compound 2 (500 mg, 2.06 mmol) was dissolved in 13 mL of anhydrous 1,4-dioxane, and to this solution was added NHS (283 mg, 2.46 mmol) and DCC (507 mg, 2.46 mmol). The reaction mixture was refluxed for 3 h. and then cooled at room temperature in order to remove the dicyclohexylurea (DCU) formed. Then, β-alanine (248 mg, 2.78 mmol was added and the mixture was heated for 20 h. at 60° C. The solution was rotoevaporated to dryness and the crude product was purified by column chromatography with chloroform as mobile phase. 230 mg of a white solid was obtained. Yield: 40%. Mp.: 180.5-181.8° C. ESI-MS (m/z)=316 (M.+1)$^+$.

Example 5: 6-{[4-(1-naphthylamino)-4-oxobutanoyl]amino}hexanoic acid (5)

2 (1 g, 4.4 mmol), DCC (0.9 g, 4.4 mmol), 6-aminocaproic acid (0.6 g, 7.6 mmol) and triethylamine (0.6 mL, 4.3 mmol) in 40 mL of DMF were refluxed for 6 hours. Then, the mixture reaction was rotoevaporated to dryness and the crude product was recrystallized from ethanol. The solid thus obtained was dried over $P_2O_5$ to yield 0.28 g of 5. Yield: 18%. Mp.: 229-231° C. ESI-MS (m/z)=344 (M.+1)$^+$.

Example 6: N1-(2-aminoethyl)-N4-(1-naphthyl) succinimide (6)

Method A (one pot): 2 (500 mg, 2.06 mmol) and NHS (283 mg, 2.46 mmol) were dissolved in 5 mL of anhydrous under dry $N_2$ atmosphere. Next, a solution of DCC (507 mg, 2.46 mmol) in 8 mL of anhydrous 1,4-dioxane were added dropwise through a pressure equalizing dropping funnel. The reaction mixture was refluxed for 2 h. and then cooled at room temperature in order to remove the dicyclohexylurea (DCU) formed. A solution of ethylenediamine (0.18 mL, 2.7 mmol) in 1 mL of 1,4-dioxane was added. The reaction mixture was stirred at room temperature for 30 min. and then cooled to precipitate a white solid that was filtered, washed with 1,4-dioxane and acetone, and air-dried to yield 584 mg of the product (98%). Recrystallization from ether yielded 85% of pure 6. Mp.: 128.9-130.5° C.

Method B: Compound 1 (2.58 g, 11.47 mmol) and ethylenediamine (7.66 mL, 11.4 mmol) in 30 ml of 1,4-dioxane were refluxed for 2 h. and then cooled at room temperature. 15 mL of diethyl ether was added to precipitate a white solid that was filtered and washed with diethyl ether to obtain 3.27 g of product. Recrystallization from acetone yielded 63% of pure 6. Mp.: 128.9-130.5° C. ESI-MS (m/z)=287 (M.+1)$^+$.

Example 7: N1-(4-aminobutyl)-N4-(1-naphthyl) succinamic (7)

Method A: Compound 2 (2.12 g, 8.72 mmol), NHS (1.42 g, 12.34 mmol) and DCC (2.54 g, 12.33 mmol) in 30 mL of anhydrous 1,4-dioxane were refluxed for 3 h. and then cooled at room temperature to remove the DCU formed. Butylenediamine (2.6 mL (26.14 mmol) was slowly dropped and the mixture reaction was stirred for 30 min. at room temperature. The mixture was rotoevaporated to dryness and the crude product re-dissolved in 10 ml of $CHCl_3$ was washed with water (3×5 mL). Next, the organic phase was dried with anhydrous $Na_2SO_4$ and rotoevaporated to dryness. Diethyl ether (10 mL) was added to precipitate in cold a white solid. Yield: 72%. Mp.: 142.2-150.8° C.

Method B: Compound 1 (1.832 g, 8.1 mmol), triethylamine (1.94 mL, 14 mmol) and 1,4-butylenediamine (1.66 mL, 16.6 mmol) in 30 mL of DMF were refluxed for 1 hour. After solvent elimination, the reaction mixture was purified by column chromatography with ethyl acetate and ethyl acetate: methanol (10:2), as mobile phases. Yield: 11%. Mp.: 142.2-150.8° C. ESI-MS (m/z)=315 (M.+1)$^+$.

Example 8: N1-[2-(methylamino)ethyl]-N4-(1-naphthyl)succinimide (8a)

A slurry of activated molecular sieves 4 Å (500 mg) and $CsOH.H_2O$ (280 mg, 1.7 mmol) in 8 mL of anhydrous DMF, was stirred for 10 minutes. Next, compound 6 (485 mg, 1.7 mmol) in 1 mL of anhydrous DMF was added to maintain stirring for 30 min. at room temperature. To this reaction mixture, $CH_3I$ (124 μL, 2 mmol) in 0.5 mL of anhydrous DMF was added and stirred for 24 h., at room temperature. The mixture was thus filtered and rotoevaporated to dryness. The crude product was washed with NaOH (1 N) and extracted with ethyl acetate. The organic phase was dried with $Na_2SO_4$ and purified by column chromatography with ethyl acetate as mobile phase. Yield: 70%. Mp.: 120° C. (dec.). ESI-MS (m/z)=300 (M.+1).

Example 9: Sodium salt of the acid methyl (2-([4-(1-naphthylamine)-4-oxobutanol]amino)ethyl)carbamoditionic (8b)

Compound 8a (299 mg, 1 mmol) was added to a suspension of NaOH (80 mg, 2 mmol) in 3 mL of dry diethyl ether. The reaction mixture was cooled in an ice bath and stirred vigorously for 30 min., to slowly drop $CS_2$ (121 μL, 2 mmol) in 0.5 mL of ether. Then, the mixture was stirred for 30 min. in cold and then, at room temperature for 2 hours. Solids were filtered and washed with dry diethyl ether. Yield: 75%. Mp.: (dec.). ESI-MS (m/z)=398 (M.+1)$^+$.

Example 10: N1-(2-aminoethyl)-N4-(1-naphthyl) succinimide-$^{131}$I (9)

Labeling with $^{131}$I: To a tube with lodogeno covered walls (the tubes were impregnated with 250 to 500 μL of a lodogeno solution (0.2 mg/mL in $CHCl_3$), under in dry nitrogen atmosphere) was added 503.2 MBq (13.6 mCi) of $^{131}$I and stirred for 10 min. at room temperature. Then 100 μL of a solution of 6 (7.7 10$^{-3}$ mol/L) in PBS (pH 8.5) was added and the reaction mixture was thus stirred for another 15 minutes. The mixture was decanted in order to remove the $^{131}$I free by filtration through filters of 3 MM Whatman paper impregnated with silver nitrate.

Example 11: 6-bromo-2-methoxynaphthalene (11)

6-Bromo-2-naphthol (10) was obtained from the reaction between 2-naphthol and molecular bromine in glacial acetic acid according to procedure described by Reddy et al. in Organic Process Research and Development, 1999, 3, 121-25.

To a solution of $Cs_2CO_3$ (7.55 g, 23.3 mmol) and 6-bromo-2-naphthol (4.6 g, 17.9 mmol) in 45 mL of acetone, $(CH_3)_2SO_4$ (2.2 mL, 23.3 mmol) was added dropwise and stirred for 30 min. at room temperature. The reaction mixture was rotoevaporated and the crude was washed with water and extracted with $CHCl_3$. The organic phase was dried with $MgSO_4$ and cooled to precipitate 4.45 g of a white solid. Yield: 91%. Mp.: 101.4-103.7° C. (lit.: 103-105° C.).

Example 12: 3-(6-methoxy-2-naphthyl)propyl 4-methylbenzenesulfonate(13)

Preparation of Grignard reagent: according to general procedure described by Kidwell et al. in Organic Synthesis, Coil., 1973, 5, 918. In particular, in this invention, the reagent obtaining process was carried out in a flask with Mg (0.363 g, 14.95 mmol) and a small crystals of $I_2$, previously flame-dried and the atmosphere replaced with dry Ar. Then, 1 mL (0.709 g, 2.99 mmol) of a solution of 11, in 3 mL of THF, was added dropwise to the flask. The reaction mixture was slowly heated to reflux until the boiling becomes spontaneous and a white sludge was formed. After that, the rest of the solution was added dropwise and refluxed for 4 h. until the formation of 12. Preparation of the catalyst $Li_2CuCl_4$: according to general procedure described by Burns et al., in J. Chem. Soc. 1997, 119, 2125-2133.

To a flask, previously flame-dried and evacuated with Ar, a solution of 1,3-propanediol di-p-tosylate (PrDiTs) (1.26 g, 3,289 mmol) in 1 mL of THF was added. Then, 1.79 mL of catalyst $Li_2CuCl_4$ was added. The reaction mixture was cooled at −30° C. and the Grignard reagent was added dropwise. Once the addition process was finished, the mixture was maintained at 8° C. for 24 h. and later at room temperature for 48 hours. The product was thus purified by column chromatography with a mixture of n-hexane: dichloromethane (100:0 to 80:20) as mobile phase. Yield: 15%. Mp.: dec. ESI-MS (m/z)=371 (M+1)*.

Example 13:
2-(3-fluoropropyl)-6-methoxynaphthalene (14)

3 mL of (bmim)($BF_4$) was added to 3 mL of a solution of $H_2O$ (90 μL, 5 mmol) in $CH_3CN$ with 13 (370 mg, 1 mmol). Then, anhydrous CsF (760 mg, 5 mmol) was added. The reaction mixture was stirred at 100° C. for 2 hours. Upon completion of the reaction, the product of interest was extracted with diethyl ether (3×5 mL). The organic phase was dried ($MgSO_4$) and concentrated to dryness to purify by column chromatography (ethyl acetate: hexane as mobile phase). Yield: 40%. Mp.: dec. ESI-MS (m/z)=219 (M+1)$^+$.

Example 14: Labeling studies and biodistribution in rats. Compound: N1-(2-aminoethyl)-N4-(1-naphthyl)succinimide-$^{131}$I (9)

Determination of partition coefficients: A solution of 9 (20 μL), prepared as described in example 10, was added to a mixture of 3 ml of n-octanol and 3 ml of distilled water. After stirring and leaving to stand the mixture, aliquots of 20 μL from each phase were taken to determine the radiometric distribution ratio by an activity meter (CRC 35R, Capintec Inc.). This procedure was repeated to the radiopharmaceutical of $^{99m}$Tc-ECD as reference, which is used for cerebral perfusion studies. Partition coefficient of 9:0.54 (log P=−0.27) and $^{99m}$Tc-ECD: 40.6 (log P=1.6).

Animal studies: A solution of 9 15 MBq (407 Ci), prepared as described above, was administered to male Wistar rats (160 g, n=3) through the lateral tail vein. Then, images were taken every 15 seconds, for 30 min. (120 images) with a gamma camera (Medis Nucline TH22, Hungary), with a peak centered at 360 keV and a window of ±25%. The image processing was performed on a processing station Segami (USA).

The invention claimed is:

1. A method of displaying the density of amyloid sheets in a mammalian brain, said method comprises:
(a) providing an isotopic label of a compound of structure II wherein;
$R_1$ is alkyl-, and
$R_2$ is -alkylenyl-arylsulfonate, -alkylenyl-halide, -alkylenyl-$NH_2$, -alkylenyl-NH-alkyl, or an -alkyl (alkylenyl)-N-dithiocarbamate salt, or alternately;
wherein;
$R_1$ is -alkylenyl-halide, or -alkylenyl-O-arylsulfonate and $R_2$ is -halide, -alkylenyl-O-arylsulfonate, -alkylenyl-O-alkylsulfonate, -alkylenylhalide, —CH(O), —HC═C(CN)$_2$, —HC═CHNO$_2$, -alkylenyl-$NH_2$, -alkylenyl-NH-alkyl or an -alkyl (alkylenyl) dithiocarbamate salt; and
wherein at least one or more of the halogen or carbon atoms are replaced by its corresponding isotopic form or at least one of the hydrogen atoms of the naphthyl ring is replaced by a halogen atom,
(b) administering the compound of step (a) to a living mammal,
wherein the compound passes the blood brain barrier of the mammal;
(c) allowing the compound administered in step (b) to be bound to amyloid sheets; and
(d) displaying the density of amyloid sheets in the mammal brain, by the detection of the isotopic label of the compound, of step (c) through an imaging technique.

2. The method according to claim 1, wherein the alkyl term in the compound of structure II is selected from the group consisting of methyl, ethyl, n-propyl, iso-propyl, n-butyl and iso-butyl, and the alkylenyl in $R_1$ and in $R_2$ of the compound of structure II is selected from the group consisting of ethylenyl (—$CH_2CH_2$—), propylenyl (—$CH_2CH_2CH_2$—) and butylenyl (—$CH_2CH_2CH_2CH_2$—).

3. The method according to claim 1, wherein the step providing an isotopic form comprises labeling the compound of structure II, wherein $R_1$ is —(CH$_2$)$_n$X (n=3, 4 or 5), X is —OSO$_2R_3$, $R_3$ is p-CH$_3C_6H_4$— and $R_2$ is a bromide.

4. The method according to claim 1, wherein the step providing an isotopic form comprises labeling the compound of structure II, wherein $R_1$ is selected from the group consisting of —CH$_3$, —C$_2H_5$, n-C$_3H_7$ and iso-C$_3H_7$, and $R_2$ is —(CH$_2$)$_n$OSO$_2C_6H_4$-p-CH$_3$ (n=3, 4 or 5).

5. The method according to claim 1, wherein $R_1$ in the compound of structure II is selected from the group consisting of —CH$_3$, —C$_2H_5$, -n-C$_3H_7$ and iso-C$_3H_7$, $R_2$ is —(CH$_2$)$_n$X (n=3, 4 or 5), X is a halide, selected from the group consisting of $^{18}$F and $^{19}$F.

6. The method according to claim 1, wherein the step providing an isotopic form comprises labeling the compound of structure II, wherein $R_1$ is —(CH$_2$)$_n$Y (n=3, 4 or 5), Y is —OSO$_2R_3$, $R_3$ is —CH$_3$ or p-CH$_3C_5H_4$— and $R_2$ is —CH(O).

7. The method according to claim 1, wherein the step providing an isotopic form comprises labeling the compound of structure II, wherein $R_1$ is —(CH$_2$)$_n$Y (n=3, 4 or 5), Y is —OSO$_2R_3$, $R_3$ is —CH$_3$ or p-CH$_3C_6H_4$— and $R_2$ is —HC═C(CN)$_2$ or —HC═CHNO$_2$.

8. The method according to claim 1, wherein $R_1$ in the compound of structure II is —(CH$_2$)$_n$X (n=3, 4 or 5), X is halide selected from the group consisting of $^{18}$F and $^{19}$F and $R_2$ is —HC═C(CN)$_2$ or —HC═CHNO$_2$.

9. The method according to claim 1, wherein $R_1$ in the compound of structure II is selected from the group consisting of —$CH_3$, —$C_2H_5$, n-$C_3H_7$ and iso-$C_3H$, and $R_2$ is selected from the group consisting of —$CH_2CH_2NH_2$, —$CH_2CH_2NHR_4$ and —$CH_2CH_2NR_4R_5$, $R_4$ is selected from the group consisting of —$CH_3$ and —$C_2H_5$, $R_5$ is —C(S)SW, W is $Na^+$, $K^+$ or a $Cs^+$.

10. The method according to claim 1, wherein at least one of the hydrogen atoms of naphthyl ring of the compound of structure II is replaced by a radioactive halogen atom selected from the group consisting of $^{123}I$ or $^{131}I$.

11. The method according to claim 1, wherein the compound of structure II with $R_1$ is selected from the group consisting of —$CH_3$, —$C_2H_5$, n-$C_3H_7$ and iso-$C_3H_7$ and $R_2$ is selected from the group consisting of —$CH_2CH_2NH_2$, —$CH_2CH_2NHR_4$ and —$CH_2CH_2NR_4R_5$, $R_4$ is —$CH_3$ or —$C_2H_5$, $R_5$ is —C(S)SW, W is $Na^+$, $K^+$ or $Cs^+$, is complexed with $^{99m}Tc$ and a chelating ligand selected from the group consisting of 2,2'-oxydiethanethiol and N1-(2-aminoethyl)-1,2-ethanediamine.

12. The method according to claim 1, wherein $R_2$ in the compound of structure II is —$CH_2CH_2NHR_4$ or —$CH_2CH_2NR_4R_5$, $R_4$ is —$CH_3$ or —$C_2H_5$, $R_5$ is —C(S)SW, W is $Na^+$, $K^+$ or $Cs^+$, and wherein at least one of the carbon atoms of $R_4$ is replaced by a $^{11}C$ radioactive isotope atom.

13. The method according to claim 1, wherein the step of displaying comprises detecting in the mammalian brain the distribution of isotopic label of the compound bound to the amyloid sheets by a diagnostic imaging technique.

14. The method according to claim 13, wherein said diagnostic imaging technique for displaying the radioisotopic label of the compound of structure II in a mammalian brain is single photon emission computed tomography (SPECT).

15. The method according to claim 13, wherein said diagnostic imaging technique for displaying the radioisotopic label of the compound of structure II in a mammalian brain is positron emission tomography (PET).

16. The method according to claim 13, wherein said diagnostic imaging technique for displaying the isotopically labeled compound with $^{19}F$ in a mammalian brain is magnetic resonance imaging (MRI).

17. The method of claim 1, wherein the living mammal is a human having Alzheimer's disease (AD), and the compound has a log P coefficient of less than 1.6, whereby the compound readily passes the blood brain barrier (BBB) and selectively binds to Alzheimer's diseased amyloid sheets of the AD.

18. The method according to claim 1, wherein $R_1$ in the compound of structure II is —$(CH_2)_nX$ (n=3, 4 or 5), X is $^{19}F$ and $R_2$ is selected from the group consisting of $^{123}I$ and $^{131}I$.

* * * * *